US007285298B2

(12) United States Patent
Gaudout et al.

(10) Patent No.: US 7,285,298 B2
(45) Date of Patent: *Oct. 23, 2007

(54) USE OF A DIHYDROCHALCONE-RICH PHENOLIC FRACTION IN A COSMETIC TREATMENT

(75) Inventors: David Gaudout, Fougeres (FR); Denis Megard, St Brice En Cogles (FR); Frédéric Lejard, Arradon (FR)

(73) Assignee: Diana Ingredients S.A., Saint Nolff, Elven (FR)

( * ) Notice: Subject to any disclaimer, the term of this patent is extended or adjusted under 35 U.S.C. 154(b) by 355 days.

This patent is subject to a terminal disclaimer.

(21) Appl. No.: 10/967,524

(22) Filed: Oct. 18, 2004

(65) Prior Publication Data

US 2005/0048149 A1   Mar. 3, 2005

Related U.S. Application Data

(62) Division of application No. 10/118,521, filed on Apr. 4, 2002, now Pat. No. 6,805,873.

(30) Foreign Application Priority Data

Feb. 26, 2002  (FR) .................................. 02 02418

(51) Int. Cl.
  A61K 36/73  (2006.01)
  A61K 8/02   (2006.01)
  A61K 47/00  (2006.01)
  A61K 31/05  (2006.01)
  C11B 5/00   (2006.01)

(52) U.S. Cl. ...................... 424/765; 424/401; 424/439; 424/489; 424/725; 424/777; 426/542; 426/615; 426/640; 426/648; 514/25; 514/731; 514/732

(58) Field of Classification Search ................ 424/765, 424/401, 439, 489, 725, 777; 426/542, 615, 426/640, 648; 514/25, 731, 732
  See application file for complete search history.

(56) References Cited

U.S. PATENT DOCUMENTS

| 4,698,360 | A | 10/1987 | Masquelier | 514/456 |
| 4,760,135 | A | 7/1988 | Diedrich et al. | 536/17.9 |
| 5,985,850 | A | 11/1999 | Falk et al. | 514/54 |
| 6,448,232 | B1 * | 9/2002 | Ehrenkranz | 514/25 |
| 6,805,873 | B2 * | 10/2004 | Gaudout et al. | 424/401 |
| 7,041,322 | B2 * | 5/2006 | Gaudout et al. | 424/765 |

FOREIGN PATENT DOCUMENTS

| EP | 283349 | 2/1988 |
| EP | 348781 | 6/1989 |
| EP | 657169 | 7/1994 |
| EP | 781544 | 7/1997 |
| EP | 1243586 | 9/2002 |
| FR | 1427100 | 12/1964 |
| FR | 2092743 | 6/1970 |
| FR | 2372823 | 11/1977 |
| FR | 2643073 | 8/1990 |
| GB | 1541469 | 12/1976 |
| WO | WO 96/18382 | 12/1995 |
| WO | WO 01/24806 | 4/2001 |
| WO | WO 01/78859 | 10/2001 |
| WO | WO 02/34073 | 5/2002 |

OTHER PUBLICATIONS

Avarado et al., "Phlorizin as a Competitive Inhibitor of the Active Transport of Sugars by Hamster Small Intestine, in vitro", Biochimica Et Biophysica Acta, 56, 1962, pp. 170-172.
Esaki, S., et al., "Synthesis of Phlorctin 2'—O-B-L-Glycosides and Their Inhibitory Action against Sugar Transport in Rat Small Intestine", Agric. Biol. Chem., 55, (11), 1991, pp. 2855-2860.
Goetsch, G.D., et al., "Effects of Oral Administration of Short-Chain Fatty Acids on Certain Blood and Urine Constituents of Fasted, Phlorhizin-Treated Ewes", American Journal Vet. Res. 19, 1958, pp. 637-641.
Schultz, L., et al., "The Effect of the Administration of Various Fatty Acids on the Blood Ketone Levels of Ruminants", Journal of Dairy Science 32, 1949, pp. 817-822.
Lyle, R., et al., "Glucose Kinetics, Plasma Metabolites, and Endocrine Responses During Experimental Ketosis in Steers", Journal of Dairy Science, 67 (10), 1984, pp. 2255-2264.
Young, J.W., et al., "Effects of Phlorizin on Glucose Kinetics in the Bovine", Journal of Dairy Science, 57, (6), 1974, pp. 689-694.
Amaral-Phillips, D.M., et al., "Nutrition, Feeding, and Calves Effects of Decreased Availability of Glucose for Dairy Cows", Journal of Dairy Science, 76, (3), 1993, pp. 752-761.
Karadeniz, F. et al., "Phenolic compounds in apple juice from different varieties", Scientific Technical Com. Int. Fed. Fruit Juice Producers, 24, 1996, pp. 265-275.
Sanoner, P., et al., "Polyphenolic profiles of French cider apple varieties", 'Polyphenols, Wine and Health', Symposium Bordeaux, France, Apr. 1999, chart.
Sanoner, P. et al., "Polyphenolic profiles of French cider apple varieties (*Malus domestica* sp.)", Journal of Agric. Food Chem., 47, (12), 1999, pp. 4847-4853.
Fiedler, et al., Arzneimittel-Forsch, 4, pp. 41-45.
Blackholly, H., "An Apple a Day Helps to Keep the Doctor Away", Nutrition and Food Science, 109, 1987, pp. 2-4.
Park, J., et al., "Intracellular Accumulation of Ascorbic Acid Is Inhibited by Flavonoides via Blocking of Dehydroascorbic Acid and Ascorbic Acid Uptakes in HL-60, U937 and Jurkat Cells", Journal of Nutrition 130, 2000, pp. 1297-1302.
Paganga, G., "The Polyphenolic Content of Fruit and Vegetables and their Antioxidant Activities. What Does a Serving Constitute?", Fre.Rad. Rev., vol. 30, pp. 153-162, 1999.
The Merck Index, Twelfth Edition, Merck Research Laboratories, pp. 1260-1261, 1996.

* cited by examiner

*Primary Examiner*—Herbert J. Lilling
(74) *Attorney, Agent, or Firm*—Elizabeth A. Galletta; Todd E. Garabedian; Wiggin and Dana LLP

(57) ABSTRACT

The use of a dihydrochalcone-rich polyphenolic fraction in the cosmetic treatment of mammals in order to limit the weight, to improve the aesthetic appearance of the body, and to treat certain non-pathological forms of obesity. The use of a dietary or nutraceutical composition based on this phenolic fraction. A composition based on this polyphenolic fraction for use as a medicinal product in the prevention of diabetes.

15 Claims, 1 Drawing Sheet

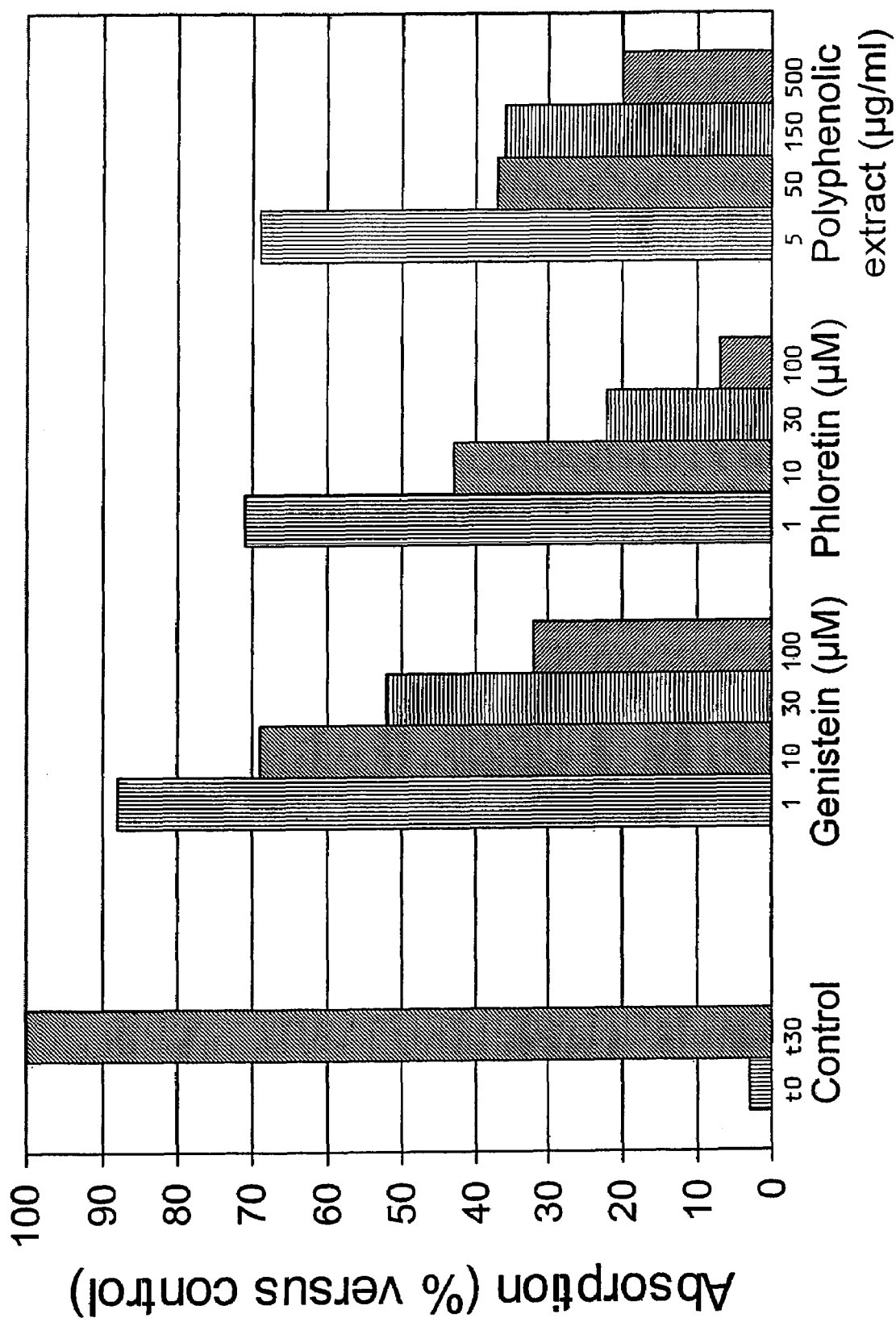

USE OF A DIHYDROCHALCONE-RICH PHENOLIC FRACTION IN A COSMETIC TREATMENT

CROSS-REFERENCE TO RELATED APPLICATIONS

This application is a divisional of U.S. patent application, Ser. No. 10/118,521 filed Apr. 4, 2002, now U.S. Pat. No. 6,805,873. The disclosure of this parent patent application is incorporated herein by reference in its entirety.

BACKGROUND OF THE INVENTION

1. Field of the Invention

The present invention relates to the use of a dihydrochalcone-rich phenolic fraction in the cosmetic treatment of mammals in order to limit the weight, to improve the aesthetic appearance of the body and to treat certain non-pathological forms of obesity. The invention also relates to the use of a dietary or nutraceutical composition based on this phenolic fraction. The present invention also discloses a composition based on this phenolic fraction for its use as a medicinal product intended to be used in the prevention of diabetes.

2. Description of the Related Art

It is known that polyphenolic compounds are very widespread in the plant kingdom. The most abundant are chlorogenc acid, procyanidins B1 and B2, epicatechin, phloretin, phloridzin. and p-coumaric acid. Consequently, many polyphenol-rich products are available on the market, the most common being extracted from green tea, from grape-seeds and from pine bark (U.S. Pat. No. 4,698,360, EP A 348 781, EP A 283 349, FR A 1 427 100, FR A 2 092 743, FR A 2 643 073 and FR A 2 372 823).

Patent EP A 0 657 169 has already disclosed the extraction of a polyphenolic fraction from unripe fruit (weighing from 3 to 10 grams) of the *Rosacea* family (apple, pear, etc.). The polyphenolic fraction thus defined is characterized by a high content of derivatives of the hydroxycinnamic acid family (chlorogenic acid, caffeic acid and p-coumaric acid) and of molecules from the flavanol family (catechin, epicatechin and procyanidin). The phloridzin of these extracts derived from unripe fruit represents less than 7% by weight off all of the phenolic compounds, and the typical dihydrochalcones (phloridzin and phloretin) of *Rosacea* plants less than 9%. Among the phenolic compounds present in the plant kingdom, phloretin and its glycosylated derivative, phloridzin, are typical of apple and of other fruits of the *Rosacea* family. Phloridzin is found in large amounts in the pips and bark of trees, and in much lower amounts in apple juice and peel. and in much lower amounts in apple juice and peel.

Phloridzin has been known for a long time for its activity in blocking the assimilation of glucose. One of the mechanisms of action. described is considered to be that phloridzin comes into competition with simple sugars and, consequently, limits their transport in the blood (Alvarado and Crane, *Biochim. Biophys. Acta*, 56, pp. 170, 1962). Another mechanism, possibly linked to the previous one, is considered to involve the blocking of the sodium-dependent transport systems of sugars such as glucose, galactose, xylose, etc., in the small intestine (Esaki et al., *Agric. Biol. Chem.*, 55, 11, pp. 2855, 1991). It appears that the 'natural' transporter of sugar has two independent sites, the site with 'sugar' affinity and the site with 'phenol' affinity, and that, by binding strongly to the transporter by interaction with the two sites, phloridzin blocks the transport of sugars across the membranes.

These hypotheses were confirmed by in vivo studies. Phloridzin has been successfully studied experimentally for a long time for reducing the availability of blood glucose and inducing glycosuria (presence of glucose in the urine) in sheep (Goetsch and Pritchard, *Am. J. Vet. Res.*, 19, pp. 637, 1958), goats (Schultz et al., *J. Dairy Sci.*, 32, pp. 817, 1949) and cattle (Lyle et al., *J. Dairy Sci.*, 67, pp. 2255, 1984; Young et al., *J. Dairy Sci.*, 57, pp. 689, 1974). 2 to 4 grams of phloridzin per day for 48 h as a subcutaneous injection in a cow are sufficient to bring about a drastic reduction in the glucose and insulin contents of the blood plasma and the excretion of 225 to 337 grams of glucose per day in the urine of the treated animal (Amaral-Phillips et al., *J. Dairy Sd.*, 76, pp. 752, 1993).

This mechanism of blocking the membrane transport of glucose is very advantageous in particular in Western diets for preventing diabetes and for treating certain forms of obesity. Thus, two patents involve phloridzin in medicinal compositions intended to block glucose transport. Patent CZ 1993000931986 (Valovic) discloses a mixture based on phosphoric acid, sulphuric acid, lactic acid, creosote, arsenic trioxide, sodium sulphate and plant extracts including phloridzin extracted from fruit tree bark. Patent U.S. Pat. No. 5,985,850 (Falk and Asculai) discloses pharmaceutical compositions involving hyaluronic acid as transporter of active molecules (including phloridzin or molecules of the same family) for blocking glucose transport in certain types of cells.

In apple homogenate or apple juice, the dihydrochalcones (phloretin and phloridzin) are present in a minor amount compared with the other polyphenols. Chlorogenic acid and procyanidins are the major polyphenols of apples, whether these are cider apples or dessert apples, phloridzin and phloretin never representing more than 5% by weight o f the total polyphenols of ripe apples (Karadeniz and Ekski, *Scientific Technical Com. Int. Fed. Fruit Juice Producers*, 24, pp. 265-275, 1996; Sanoner et al., Polyphenolic profiles of French cider apple varieties. In 'Polyphenols, wines and health', Symposium, Bordeaux, 14-16 April, 1999; Sanoner et al., *J. Agric. Food Chem.*, 47, pp. 4847-4853, 1999).

In the known polyphenolic extracts, the proportions between the various phenolic molecules are retained relative to the proportions present in the various starting materials. Polyphenolic extracts rich in hydroxycinnamic acids (caffeic acid, chlorogenic acid and p-coumaric acid) and poor in dihydrochalcones (phloridzin and phloretin) are thus conventionally obtained:

| Phenolic compound | Apple* (in mg/L of juice or mg/kg of homogenate) | Known polyphenolic extract of apple (in mg/kg of powder) |
|---|---|---|
| Ceffeic acid | ϵ | 21.7 |
| Catechin | ϵ to 150 | 15.1 |
| Chlorogenic acid | 60 to 1200 | 161.0 |
| Procyanidins | 500 to 5,000 | 69.6 (B1 and B2) |
| p-Coumaric acid | 1 to 150 | 9.3 |
| Epicatechin | ϵ to 1,400 | 41.4 |
| Phloridzin | 6 to 100 | 32.7 |
| Quercitrin | ϵ | 1.9 |

-continued

| Phenolic compound | Apple* (in mg/L of juice or mg/kg of homogenate) | Known polyphenolic extract of apple (in mg/kg of powder) |
|---|---|---|
| Phloretin | 5 to 100 | 9.5 |
| Total polyphenols (expressed as phloridzin equivalent) | | 483.4 |

ε = unquantifiably low amount
*values compiled from measurements on 15 varieties of cider apples and 3 varieties of dessert apples over 3 harvests (Karadeniz and Ekski).

Caffeic acid is in fact a decomposition product of chlorogenic acid, since there is only very little caffeic acid, indeed even none at all, naturally present in apples (Fiedler, *Arzneimittel-Forsch*, 4, pp. 41, 1954).

The disclosures of the documents listed in this section and elsewhere throughout this application are incorporated herein by reference.

SUMMARY OF THE INVENTION

The Applicant has become interested in. a phenolic fraction of apple, apples being well known for their beneficial effects on the health (Blackholly, *Nut. and Food Sci.*, 109, pp. 2-4, 1987). The Applicant has developed the cosmetic use of dihydrochalcone-rich phenolic fractions, which constitutes the subject of the invention.

One aspect of the invention is related to a medicinal composition that includes an excipient and at least one dihydrochalcone-rich polyphenolic fraction. The fraction is obtained from fruit of the Rosacea family and comprises at least 10% by weight of polyphenols, and at least 10% by weight of the total polyphenols is phloridzin.

Another subject consists of the uses of this fraction as a dietary, nutraceutical, or cosmetic supplement in a cosmetic treatment for improving the aesthetic appearance of the body.

Other subjects will become apparent on reading the description and the examples which follow.

BRIEF DESCRIPTION OF THE DRAWING

The Figure shows the inhibition of absorption of 2-deoxyglucose by a human uterine cell line with different inhibitors after incubation for 30 minutes in a physiological medium.

DETAILED DESCRIPTION OF THE INVENTION

One subject of the present invention is, in the cosmetic treatment of mammals, the use of dihydrochalcone-rich polyphenolic fractions from fruit of the *Rosacea* family. These dihydrochalcone-rich phenolic fractions have excellent properties in terms of regulating carbohydrate metabolism, and more specifically the property of reducing the assimilation of saccharides, especially of glucose, by blocking the saccharide transport systems. In the context of a cosmetic treatment for improving the aesthetic appearance of the body, they play an active role in limiting the weight, in controlling weight gain and in certain non-pathological forms of obesity.

The use of these fractions in dietary or nutraceutical preparations for limiting the weight, for controlling weight gain and for certain non-pathological forms of obesity constitutes the subject of the invention.

The dilydrochalcone—rich polyphenolic fractions used in the invention includes an excipient and at least 10% by weight of polyphenols and preferably 50%, at least 10% by weight of which is composed of phloridzin and preferably between 10% and 70%. These extracts can also contain chlorogenic acid, epicatechin, procyanidins, quercitrin,p-coumaric acid and phloretin.

One composition that is particularly preferred of these polyphenolic fractions is that they contain, by weight:
more than 10% and preferably more than 50% of total polyphenols,
at least 30% and preferably from 30% to 40% by weight of the polyphenols as phloridzin,
not more than 11% and preferably between 2% and 11% of the polyphenols as chlorogenic acid,
not more than 4% of the polyphenols as epicatechin,
not more than 2% of the polyphenols as procyanidin B2,
not more than 2% of the polyphenols as quercitrin,
not more than 2% of the polyphenols as quercitrin,
not more than 0.5% of the polyphenols as p-coumaric acid, and
less than 0.5% of the polyphenols as caffeic acid.

The polyphenolic fractions are characterized in that the dihydrochalcones are present in proportions of greater than or equal to 40% by weight relative to the hydroxycinnamic acids.

The caffeic acid is present in weight proportions of less than. 20% of the weight of phloridzin present. Preferably, the caffeic acid represents less than 1% by weight of the total polyphenols of the extracts.

The proportion of phloridzin is 9 times as great by weight as that of the catechin.

The amount of phloridzin present is at least equivalent by weight to that of the chlorogenic acid.

The polyphenolic fractions that may be used for the intended application may contain phloretin: by means of a controlled acid hydrolysis (Merck Index, 12th Edition), virtually all of the phloridzin can be converted into phloretin.

In the phenolic fractions according to the invention, the dihydrochalcones are present in proportions of greater than or equal to 40% by weight relative to the hydroxycinnamic acids.

The dihydrochalcone-rich polyphenolic fractions used in the invention may be obtained by the following extraction process for selectively extracting a dihydrochalcone-rich polyphenolic fraction from ripe apples:
The crushed apples are subjected to one or more solid/liquid extractions, in the presence or absence of added water.
The wet solid extract obtained is then either dried or enzymatically liquefied to obtain a liquid extract.
The dry solid extract undergoes further extractions over a period of between 10 minutes and 2 hours with a polar organic solvent, preferably a C1-C4 aliphatic alcohol, pure or as a mixture with water, to obtain an organic extract.
This organic extract is evaporated to dryness at: a temperature of less than or equal to 60° C., preferably under reduced pressure.
This residue is then taken up in water, after which it is extracted several times, preferably 4 times, with a water-immiscible solvent, preferably ethyl acetate or methyl or propyl acetate.
The organic solutions obtained are mixed together and evaporated to dryness at a temperature of less than 60° C., and preferably less than 50° C., to obtain the polyphenolic fraction which is the subject of the present invention.
Via another route, the wet solid extract is mixed with water in the presence of an enzymatic mixture for a period of between 1 and 4 hours at a temperature of between 30 and 50° C., and preferably between 40 and 45° C., to obtain a liquid extract.

This liquid extract is clarified by centrifugation or by filtration and then by ultrafiltration.

The extract is loaded onto a chromatography column filled with an adsorbent resin of styrenedivinylbenzene type. The resin is washed with acidified water to remove the impurities and the residual sugars. The polyphenols are then eluted with an aqueous-alcoholic solution containing between 40% and 70% and preferably between 50% and 60% by weight of ethanol. Other C1-C4 aliphatic alcohols may be used, such as methanol or butanol.

If necessary, a dewaxing step is introduced during the process.

The product obtained by extraction is taken up a final time in water and then dried, preferably by atomization or lyophilization, to give a beige-coloured powder containing at least 20% by weight of polyphenols, preferably more than 50% of polyphenols, 10% by weight, and preferably between 10% and 70%, of the polyphenols of which are dihydrochalcones, preferably phloridzin.

The fractions are obtained by the process described above, preferably from ripe apples of the *Rosacea* family and in particular of the species *Malus sylvestris* Mill.

This extract of eating apples having the characteristics stated, obtained according to the process described above, may be used as a dietary or nutraceutical supplement.

A subject of the invention is also the use of a cosmetic composition comprising, inter alia, the dihydrochalcone-rich polyphenolic fraction described above.

A subject of the invention is also the use of 'a dietary composition for cosmetic treatment in order to limit the weight, for the cosmetic treatment of certain non-pathological forms of obesity and to improve the aesthetic appearance of the body.

By substantially reducing the absorption of sugars by the tissues, the polyphenolic extract has a beneficial role in controlling excess weight and obesity, and can thus be advantageously used in nutraceutical or dietary products intended for 'slimming'.

The invention also relates to a therapeutic composition containing at least one dihydrochalcone-rich polyphenolic fraction as defined above, for its use as a medicinal product, this medicinal product being intended to be used in the prevention of diabetes.

The compositions according to the invention may be administered externally or internally. Depending on the mode of administration, the composition according to the invention may be in any form usually used in cosmetics, such as, for example, supplemented dietary products, gel capsules or beverages.

The nutraceutical, dietary or cosmetic compositions of the present invention are conventionally formulated according to the application for which they are intended.

The examples that follow illustrate the invention without limiting it in any way.

EXAMPLE 1

Activity on Inhibiting Glucose Transport by the Phloridzin-Rich Polyphenolic Fraction The membrane-bound glucose transporters (GLUTs) are universal transporters of glucose and dehydroascorbic acid (DHAA) in mammalian cells and are essential for the metabolism of sugars.

The measurement of the efficacy of the polyphenolic extract to block a sugar transporter to inhibit the absorption both of glucose and. of DHAA uses a method described by Park and Levine (*J. Nutr.*, 130, pp. 1297-1302, 2000). This method involves the GLUT1 transporter, which exists in most tissues. The activation of this transporter allows glucose to be transported from the blood into cells.

We used a human uterine cell line (Ishikawa Var 1) to study the effect of the polyphenolic extract at concentrations of between 5 and 500 µg/ml on the response to the absorption of glucose. The experiments are performed in a physiological saline to minimize the artefacts associated with possible binding with proteins. The response is measured after incubation for 30 minutes by using a labelled 2-deoxyglucose (2DeOG) and the results are compared with known glucose-transporter inhibitors, that is to say phloretin and genistein. The results are expressed in graph form as the percentage of inhibition of the transport of 2DeOG after incubation for 30 minutes, relative to the control without inhibitor (which is shown pre-incubation, as t0, and post-incubation, as t30), in the Figure.

The polyphenolic extract shows a very large effect of inhibition of the membrane transport of glucose, irrespective of the concentrations between 5 and 500 µg/ml: there is an approximately 30% inhibition of the absorption of 2DeOG at a concentration of µg/ml, and this inhibition rises to 80% for a concentration of 500 µg/ml. The effect of the polyphenolic extract is at least equivalent to, indeed even greater than, that of genistein or phloretin at concentrations of between 1 and 100 µM, which are concentrations that are generally recognized for their efficacy with respect to the desired effect.

This experiment thus shows that the dihydrochalcone-rich polyphenolic fraction contributes towards controlling the sugar uptake by the body, promoting the control of excess weight, and going as far as preventing certain forms of diabetes.

EXAMPLE 2

Formulation of a Gel Capsule for Nutraceutical Use 24 milligrams of the polyphenolic extract according to the invention are incorporated into a 400-milligram gel capsule. The remaining 376 milligrams are apple pectin.

The amount of polyphenolic extract according to the invention present in the gel capsule thus formulated corresponds to the supply of the equivalent amount of dihydrochalcones contained in one apple.

EXAMPLE 3

Formulation of a Nutraceutical Dietary Product

The white mass of yoghurt contains from 2° % to 7% of added sugars and a fat content of between 3% and 5% of the crude mass of the yoghurt. The pH of this yoghurt is between 4.1 and 4.3.

A fruit-flavoured. yoghurt containing from 8% to 10% of fruit in the white mass is prepared. The polyphenolic extract according to the invention is directly incorporated into the fruit preparation (at the same time as the flavourings and colorants) intended for the yoghurt. However, since the dihydrochalcones are molecules that are not very soluble, 24 mg of polyphenolic extract may be predissolved in 0.5 ml of an aqueous-alcoholic solution before being incorporated into the fruit preparation intended for the yoghurt. or directly into the yoghurt.

At this dose, the polyphenolic extract has no negative organoleptic effect. In addition, the labelling can claim a 100% apple formulation if, in addition to the use of apple purées and/or apple juice concentrates, the flavouring is produced using an essence of apple and the sugar supply is provided by apple sugar.

A low-calorie fresh dairy product is thus obtained.

The foregoing detailed description is offered primarily for purposes of illustration. It will be readily apparent to those skilled in the art that the precise parameters of the invention described herein may be further modified or substituted in various ways without departing from the spirit and scope of the invention; and all such modifications and substitutions are within the scope of this invention.

We claim:

1. A medicinal composition comprising an excipient and at least one dihydrochalcone-rich polyphenolic fraction where the fraction is obtained from fruit of the Rosacea family and comprises at least 10% by weight of polyphenols, wherein 10% to 70% by weight of the total polyphenols is phloridzin.

2. The composition of claim 1 where the fraction further comprises chlorogenic acid and the weight ratio of phloridzin to chlorogenic acid is greater than or equal to 1.

3. The composition of claim 1 where the fraction further comprises epicatechin and the weight ratio of phloridzin to epicatechin is greater than 9.

4. The composition of claim 1 where the fraction further comprises minor amounts of procyanidin B2, quercitrin, quercitrin, p-coumaric acid and other phenols.

5. The composition of claim 1 where the fraction further comprises caffeic acid and the weight ratio of phloridzin to caffeic acid is greater than 4.

6. The composition of claim 1 where the fraction further comprises caffeic acid, and less than 1% by weight of the total polyphenols is caffeic acid.

7. The composition of claim 1 where the fraction further comprises phloretin.

8. The composition of claim 1 where the fraction comprises phloridzin, phloretin, caffeic acid, chlorogenic acid, and p-coumaric acid; and the weight ratio of (phloridzin+phloretin) to (caffeic acid+chlorogenic acid+p-coumaric acid) is greater than or equal to 40%.

9. The composition of claim 1 where the fraction is extracted from ripe apples.

10. The composition of claim 1 where the fraction is extracted from Malus sylvestris Mill apples.

11. The composition of claim 1 wherein the fraction contains more than 50% by weight of the total polyphenols in the fruit.

12. The composition of claim 1 wherein at least 30% by weight of the total polyphenols is phloridzin.

13. The composition of claim 12 wherein from 30% to 40% of the total polyphenols is phloridzin.

14. The composition of claim 1 wherein the composition is in the form of a supplemental dietary product, a gel capsule or a beverage.

15. The composition of claim 1 wherein at least a portion of the phloridzin is in the form of phloretin.

* * * * *